US007393994B2

(12) United States Patent
Masliah et al.

(10) Patent No.: US 7,393,994 B2
(45) Date of Patent: Jul. 1, 2008

(54) TRANSGENIC MOUSE MODEL FOR NEURODEGENERATIVE DISEASES

(75) Inventors: Eliezer Masliah, San Diego, CA (US); Edward Rockenstein, Chula Vista, CA (US); Margaret E. Mallory, Encinitas, CA (US)

(73) Assignee: Regents of the University of California, Oakland, CA (US)

( * ) Notice: Subject to any disclaimer, the term of this patent is extended or adjusted under 35 U.S.C. 154(b) by 1097 days.

(21) Appl. No.: 09/933,640

(22) Filed: Aug. 20, 2001

(65) Prior Publication Data

US 2003/0056231 A1    Mar. 20, 2003

Related U.S. Application Data

(63) Continuation-in-part of application No. PCT/US01/05569, filed on Feb. 20, 2001.

(60) Provisional application No. 60/183,571, filed on Feb. 18, 2000.

(51) Int. Cl.
*G01N 33/00* (2006.01)
*A01K 67/027* (2006.01)

(52) U.S. Cl. ............................................. 800/3; 800/18
(58) Field of Classification Search ..................... 800/3, 800/18
See application file for complete search history.

(56) References Cited

U.S. PATENT DOCUMENTS 4,736,866 A   4/1988  Leder
5,574,206 A   11/1996 Jolicoeur

OTHER PUBLICATIONS

Houdebine, LM (1994) Production of pharmaceutical proteins from transgenic animals. J. Biotechnology 34: 269-287.*
Kappel et al. (1992) Regulating gene expression in transgenic animals. Curr. Opin. in Biotechnology 3: 548-553.*
Sigmund, CD (2000) Viewpoint: Are studies in genetically altered mice out of control? Arterioscler. Thromb. Vasc. Biol. 20: 1425-1429.*
Strojek and Wagner (1988) The use of transgenic animal techniques for livestock improvement. Genetic Engineering: Principles and Methods 10: 221-246.*
Wall, RJ (1996) Transgenic livestock: Progress and prospects for the future. Theriogenology 45: 57-68.*
Boggio et al. (1998) Interleukin 12-mediated prevention of spontaneous mammary adenocarcinomas in two lines of Her-2/neu transgenic mice. J. Exp. Med. 188(3): 589-596.*
Geng et al. (1998) Widespread expression of an autoantigen-GAD65 transgene does not tolerize non-obese diabetic mice and can exacerbate disease. Proc. Natl. Acad. Sci. USA 95: 10055-10060.*
Andrää, K., Abramowski, D., Duke, M., Probst, A., Wiederhold, K.-H., Büürki, K., Goedert, M., Sommer, B. & Staufenbiel, M.

(1996) Expression of APP in transgenic mice: a comparison of neuron-specific promoters. *Neurobiol. Aging* 17, 183-190.
Borchelt DR, Davis J, Fischer M, Lee MK, Slunt HH, Ratovitsky T, Regard J, Copeland NG, Jenkins NA, Sisodia SS, Price DL. (1996) A vector for expressing foreign genes in the brains and hearts of transgenic mice. *Genet. Anal.* 13:159-63.
Carlson, G.A., Borchelt, D.R., Dake, A., Turner, S., Danielson, V., Coffin, J.D., Eckman, C., Meiners, J., Nilsen, S.P., Younkin, S.G. and Hsiao (1997) Genetic modification of phenotypes produced by amyloid precursor protein overexpression in transgenic mice. *Hum. Mol. Gen.* 6:1951-9.
Games, D., Adams, D., Alessandrini, R., Barbour, R., Berthelette, P., et al. (1995) Alzheimer-type neuropathology in transgenic mice overexpressing V717F beta-amyloid precursor protein. *Nature* (London) 373, 523-528.
Giasson, B.I., Duda, J.E., Murray, I.V., Chen, Q., Souza, J.M., Hurtig, H.I., Ischiropoulos, H., Trojanowski, J.Q., Lee, V.M. (2000) Oxidative damage linked to neurodegeneration by selective alpha-synuclein nitration in synucleinopathy lesions. *Science* 290:985-9.
Hashimoto, M., Hsu, L.J., Xia, Y., Takeda, A., Sisk, A., Sundsmo, M. and Masliah, E. (1999) Oxidative stress induces amyloid-like aggregate formation of NACP/α-synuclein in vitro. *Neuroreport* 10:717-21.
Higgins, L. S., Rodems, J. M., Catalano, R., Quon, D. & Cordell, B. (1995) Early Alzheimer's disease-like histopathology increases in frequency with age in mice transgenic for β-APP751. *Proc. Natl. Acad. Sci. USA* 92, 4402-4406.
Holtzman, D.M., Bales, K.R., Tenkova, T., Fagan, A.M., Parsadanian, M., Sartorius, L.J., Mackey, B.M., Olney, J., McKeel, D., Wozniak, D. and Paul, S.M. (2000) Apolipoprotein E isoform-dependent amyloid deposition and neuritic degradation in a mouse model of Alzheimer's disease. *Proc. Natl. Acad. Sci.* 97:2892-7.
Hsia, A.Y., Masliah, E., McConlogue, L., Yu, G.-Q., Tatsuno, G., Hu, K., Kholodenko, D., Malenka, R.C., Nicoll, R.A. and Mucke, L. (1999) Plaque independent disruption of neural circuits in Alzheimer's disease mouse models. *Proc Natl. Acad. Sci. USA* 96:3228-33.
Hsiao KK, Borchelt DR, Olson K, Johannsdottir R, Kitt C, Yunis W, Xu S, Eckman C, Younkin S, Price D, et al.(1995) Age-related CNS disorder and early death in transgenic FVB/N mice overexpressing Alzheimer amyloid precursor proteins. *Neuron* 15:1203-18.

(Continued)

*Primary Examiner*—Anne-Marie Falk
(74) *Attorney, Agent, or Firm*—Morrison Foerster LLP

(57) ABSTRACT

Alzheimer's disease, Parkinson's disease and Lewy body disease are the most commonly found neurodegenerative disorders in the elderly. The invention is a transgenic mouse that contains two transgenes, human α-synuclein and human amyloid precursor protein, which are responsible for the formation of the neuritic plaques, Lewy bodies and neurodegeneration seen in the above mentioned diseases. The transgenic mouse is an accurate model for disease by both functional and pathological assays.

20 Claims, 2 Drawing Sheets

OTHER PUBLICATIONS

Hsiao, K., Chapman, P., Nilsen, S., Eckman, C., Harigaya, Y., Younkin, S., Yang, F. & Cole, G. (1996) Correlative Memory Deficits, Aβ Elevation, and Amyloid Plaques in Transgenic Mice. *Science* 274: 99-102.

Kammesheidt, A., Boyce, F. M., Spanoyannis, A. F., Cummings, B. J., Ortegon, M., Cotman, C., Vaught, J. L. & Neve, R. L. (1992) Deposition of beta/A4 immunoreactivity and neuronal pathology in transgenic mice expressing the carboxyl-terminal fragment of the Alzheimer amyloid precursor in the brain. *Proc. Natl. Acad. Sci. USA* 89, 10857-10861.

Kang J, Lemaire HG, Unterbeck A, Salbaum JM, Masters CL, Grzeschik KH, Multhaup G, Beyreuther K, Muller-Hill B. (1987) The precursor of Alzheimer's disease amyloid A4 protein resembles a cell-surface receptor. *Nature* 325:733-6.

Lamb, B. T., Sisodia, S. S., Lawler, A. M., Slunt, H. H., Kitt, C. A., Kearns, W. G., Pearson, P. L., Price, D. L. & Gearhart, J. D. (1993) Introduction and expression of the 400 kilobase amyloid precursor protein gene in transgenic mice *Nat. Genet.* 5, 22-30.

Masliah, E., Rockenstein, E.M., Veinbergs, I., Mallory, M., Hashimoto, M., Takeda, A., Sagara, Y., Sisk, A., Mucke, L. (2000) Dopaminergic loss and inclusion body formation in alpha-synuclein mice: Implications for neurodegenerative disorders. *Science* 287:1265-9.

Morris R. (1984) Developments of a water-maze procedure for studying spatial learning in the rat. *J. Neurosci. Meth.* 11:47-60.

Mucke, L., Masliah, E., Johnson, W. B., Ruppe, M. D., Alford, M., Rockenstein, E. M., Forss-Petter, S., Pietropaolo, M., Mallory, M. & Abraham, C. R. (1994) Synaptotrophic effects of human amyloid beta protein precursors in the cortex of transgenic mice *Brain Res.* 666, 151-167.

Mucke, L., Abraham, C.R., Ruppe, M.D., Rockenstein, E. M., Toggas, S.M., Mallory. M., Alford, M. and Masliah, E. (1995) Protection against HIV-1 gp120-induced brain damage by neuronal overexpression of human amyloid precursor protein (hAPP) *J.Exp.Med.* 181: 1551-56.

Mucke, L., Masliah. E., Yu, G.-Q., Mallory, M., Rockenstein, E.M., Tatsuno, G., Hu, K., Kholodenko, D., Johnson-Wood, K. and McConlogue, L. (2000) High-level neuronal expression of abeta 1-42 in wild-type human amyloid protein precursor transgenic mice: synaptotoxicity without plaque formation *J. Neurosci.* 20:4050-8.

Quon, D., Wang, Y., Catalano, R., Scardina, J. M., Murakami, K. & Cordell, B. (1991) Formation of beta-amyloid protein deposits in brains of transgenic mice *Nature* (London) 352:239-241.

Rockenstein EM, McConlogue L, Tan H, Power M, Masliah E, Mucke L (1995) Levels and alternative splicing of amyloid beta protein precursor (APP) transcripts in brains of APP transgenic mice and humans with Alzheimer's disease. *J. Biol. Chem.* 270:28257-28267.

Strittmatter, W. J., Saunders, A. M., Schmechel, D., Pericak-Vance, M., Enghild, J., Salvesen, G. S. & Roses, A. D. (1993) Apolipoprotein E: High-Avidity Binding to β-Amyloid and Increased Frequency of Type 4 Allele in Late-Onset Familial Alzheimer Disease. *Proc. Natl. Acad. Sci. USA* 90:1977-81.

Sturchler-Pierrat, C., Ambramowski, D., Duke, M., Wiederhold, K.H., et al. (1997) Two amyloid precursor protein transgenic mouse models with Alzheimer disease-like pathology. *Proc. Natl. Acad. Sci. USA* 94:13287-92.

Cole et al., Society for Neuroscience Abstracts (1999) 25:298.

Goldberg et al., Society for Neuroscience Abstracts (1999) 25:2055.

Hashimoto et al., Brain Research (1998) 799:301-306.

International Search Report for PCT/US01/05569, mailed on Aug. 6, 2001, 2 pages.

Jensen et al., Biochem. Journal (1997) 323:539-546.

Mucke et al., Society for Neuroscience Abstracts (1999) 25:302.

Takeda et al., American Journal of Pathology (1998) 152:367-372.

Iwai et al., Biochimica et Biophysica Acta (2000) 1502:95-109.

Krueger et al., Journal of Neural Transmission (2000) 107:31-40.

\* cited by examiner

TRANSGENIC MOUSE MODEL FOR NEURODEGENERATIVE DISEASES

CROSS-REFERENCE TO RELATED APPLICATIONS

This application is a continuation-in-part of International Application No. PCT/US01/05569, filed Feb. 20, 2001, which claims benefit of priority to U.S. Provisional patent application Ser. No. 60/183,571, filed Feb. 18, 2000.

GOVERNMENT INTEREST

The invention was made with government support from the National Institutes of Health under grant number AG10869.

FIELD OF THE INVENTION

This invention relates to transgenic mice for use in the study of neurodegenerative diseases.

BACKGROUND

Alzheimer's disease (AD), Parkinson's disease (PD) and Lewy Body disease (LBD) are the most commonly found neurodegenerative disorders in the elderly. Although their incidence continues to increase, creating a serious public health problem, to date these disorders are neither curable nor preventable. There is a genetic component to these diseases, however most cases arise spontaneously in the population in the absence of mutations. Nerve damage results from the development of protein aggregates composed of proteins normally expressed in the brain. It is not known what causes the conversion of normally non-toxic proteins to their toxic state.

Recent epidemiological studies have demonstrated a close clinical relationship between AD and PD, as about 30% of Alzheimer's patients also have PD. Compared to the rest of the aging population, patients with AD are more likely to develop concomitant PD. Furthermore, PD patients that become demented usually have developed classical AD.

Although each neurodegenerative disease appears to have a predilection for specific brain regions and cell populations, resulting in distinct pathological pictures, PD, AD and LBD also share common pathological hallmarks. Patients with familial AD, Down syndrome and sporadic AD develop Lewy bodies on the amygdala which are the classical neuropathological hallmarks of PD. Additionally, each disease is associated with the degeneration of neurons, interneuronal synaptic connections and eventually cell death, the depletion of neurotransmitters, and abnormal accumulation of misfolded proteins, the precursors of which participate in normal central nervous system function.

Biochemical studies have confirmed the link between AD, PD and LBD. The central component of Lewy bodies is α-synuclein, also known as NACP (Non-amyloid component precursor). A proteolytic fragment of NACP, known as NAC, is a key component of amyloid plaques in AD. This suggests that α-synuclein plays a role in the pathogenesis of both AD and PD.

These findings have lead to the development of a new classification of neurodegenerative disorders denominated Lewy body disease (LBD). Patients with LBD are characterized by dementia, parkinsonism, psychiatric alterations, deposition of amyloid, and formation of Lewy bodies (LBs) with filamentous characteristics. LBs are the pathogenic hallmark of both PD and LBD. Although there are several animal models that mimic some aspects of AD and others that mimic some aspects of PD, there are no models that combine the characteristics of AD and PD, as seen in LBD.

The neuritic plaques that are the classic pathological hallmark of AD are composed essentially of Aβ, a 39-43 amino acid (aa) proteolytic product of the Alzheimer's amyloid precursor protein (APP), and NAC, a 35 aa proteolytic fragment of the NACP protein. Both Aβ and NAC were first identified in amyloid plaques as proteolytic fragments of their full length proteins, for which the full length cDNAs were identified and cloned. The cloning of APP (Kang et al., 1987) lead to a burst of research in which a number of mutations in AD were found that were associated with familial forms of AD including mutations at K670N/M671L (Swedish mutation), V717I (London mutation), V717F (Indiana mutation), presenilin 1 and presinilin 2. (Note, mutations are denoted by the wild type amino acid, the number of the amino acid at which the mutation is found and the amino acid that is found in the mutant form of the protein.) These mutations seem to alter the processing of APP preferentially to the $A\beta_{1-42}$ proteolytic fragment, which has a propensity to form aggregates that are pathogenic. However, such mutations cannot account for the majority of Alzheimer's patients in whom the disease arises spontaneously.

APP is expressed abundantly in synapses under normal conditions, is well conserved across species, and has been implicated in neural plasticity, learning, and memory. APP has three alternative splice variants in which exons 7 and 8 (hAPP695), exon 8 (hAPP751) or no exons (hAPP770) are spliced out of the full length transcript. The ratio of the three forms varies between regions of the brain and in normal vs. disease states; however, no definitive pattern of normal vs. abnormal has been determined (Rockenstein et al., 1995). It is not known what regulates the differential splicing of the transcript, but evidence suggests that splicing within neurons can be regulated by factors that influence neuronal differentiation and activity. Additionally, APP is processed into proteolytic fragments $A\beta_{39-43}$ under normal conditions. Disease results from an imbalance in the production of the fragments, biasing the overproduction of the proteolytic fragments, especially those that can initiate the formation of aggregates (i.e. $A\beta_{1-42}$).

α-Synuclein is part of a large family of proteins including β- and γ-synuclein and synoretin. As with APP, α-synuclein is expressed in the normal state in synapses and is believed to play a role in neural plasticity, learning and memory. Mutations in human (h)α-synuclein that enhance the aggregation of α-synuclein have been identified (A30P and A53T) and are associated with rare forms of autosomal dominant forms of PD. The mechanism by which these mutations increase the propensity of α-synuclein to aggregate are unknown.

Despite the fact that a number of mutations can be found in APP and α-synuclein in the population, most cases of AD and PD arise spontaneously. The most frequent sporadic forms of these diseases are associated with an abnormal accumulation of Aβ and α-synuclein, respectively. However, the reasons for overaccumulation of these proteins is unknown. Aβ is secreted from neurons and accumulates in extracellular amyloid plaques. Additionally Aβ can be detected inside neurons. α-Synuclein accumulates in intraneuronal inclusions called Lewy bodies. Although the two proteins are typically found together in extracellular neuritic AD plaques, they are also occasionally found together in intracellular inclusions.

Studies have been performed to analyze the processing of the non-toxic precursor proteins to their toxic proteolytic products, both in tissue culture systems and using purified proteins. Aggregates may be formed in nerve cell cultures by overexpression of α-synuclein. Overexpression of wild-type APP does not cause formation of extracellular protein aggregates in culture; however, overexpression of the Swedish APP mutation, the most pathogenic of the APP mutations, does. Aggregates may also be formed in response to oxidative stress in cell culture in cells overexpressing α-synuclein, suggesting that it may be important in the development of disease. Additionally, purified Aβ and NAC peptides are able to form aggregates in vitro, either alone or mixed, under identical conditions of temperature and pH.

Attempts to establish animal models of AD, PD and LBD have been disappointing. Initially, animals expressing transgenic APP failed to show extensive AD-type neuropathology (Kammesheidt et al., 1992; Lamb et al., 1993; Mucke et al., 1994; Higgins et al., 1995; Andrää et al., 1996). This was likely due to low levels of protein expression. Games et al. (1995) were able to generate a transgenic mouse that showed some AD-type pathology due to the high level of expression of a mutant APP (V717F) driven by a PDGF-β promoter. The transgenic animals did exhibit deposits of human Aβ in the hippocampus, corpus callosum and the cerebral cortex, but in no other regions of the brain. Plaques were observed, but there were no neurofibrilary tangles. The author stated that such results were expected as neurofibrilary tangles did not exist in rodents.

Transgenic mice expressing the Swedish double mutation (670/671) or the Swedish mutation in conjunction with the London mutation (V717I) under control of the Thy1 expression cassette were also generated (Sturchler-Pierrat et al., 1997). The age of development of plaques varied from 6 months to more than two years in each of the mice strains, and seemed to correlate well with expression levels of the proteins. Lower expression levels were required to induce pathological changes associated with disease in the animals carrying both the Swedish and Indiana mutations. However, neither animal was a full and accurate representation of the disease. Plaque formation accompanied by neuritic changes, dystrophic cholinergic fibers and inflammation were observed in the hippocampus and neocortex, but not in other brain regions. In a separate study using transgenic mice expressing the Swedish mutant form of APP under the PrP-promotor (Hsiao et al., 1996), mice were found to have normal learning and memory at 3 months, but showed impairment by 9 or 10 months. Plaques were observed in the cortical and limbic areas in these transgenic mice and a 14-fold increase in $A\beta_{1-42/43}$ was observed.

As $A\beta_{1-42}$ was known to be one of the strongly causative factors in AD, Mucke et al. (2000) created a transgenic mouse that expressed only the toxic fragment of APP, $A\beta_{1-42}$. Expression of the $A\beta_{1-42}$ fragment was toxic to the cells, but no plaques were formed, suggesting a plaque independent role for $A\beta_{1-42}$ in the progression of AD.

Additionally, transgenic animals expressing APP were found to display a variety of neurological problems including learning deficits, disturbed behavior and seizures. Again, the severity of neurological dysfunction seemed to be tied to the level of expression of the APP protein. Differences could also be attributed to the regions of the brain in which APP was expressed due to differences in promoters, integration into the genome, etc. As with the physiological symptoms though, neurological dysfunction in these animals resembled some aspects, but not all, of those seen in AD, PD and LBD. The lack of an animal model for the diseases was clearly not due to a lack of effort, but instead due to an inability to induce all of the changes that occur in the disease state.

The effect of the expression of the transgenic sequence was also largely dependent on the strain of mice in which the mutant gene was expressed. For example, concentrations of APP that produce plaques in outbred transgenic lines were found to be lethal in inbred FVB/N or C57BL/6J mice (Carlson, et al., 1997). Lines of FVB/N mice expressing low enough levels of APP695 to be viable were found to develop a CNS disorder that included neophobia, impaired spatial alternation, with diminished glucose utilization and astrogliosis mainly in the cerebrum (Hsiao et al., 1995). A similar syndrome is known to occur in about 20% of non-transgenic mice of the same strain, suggesting that the APP promotes a tendency already present in the strain.

Attempts were made to generate more accurate models of AD by crossing strains of transgenic mice to alter the pathology of the disease. Overexpression of the fibroblast growth factor 2 gene (FGF2) in transgenic mice overexpressing APP made APP more lethal, but did not alter the symptoms seen. Holtzman et al (2000) generated a number of bigenic mice by crossing transgenic mice expressing the V717F mutant of APP with mice expressing various forms of apolipoprotein E (apoE). The ε4 allele of apoE was the first genetic risk factor identified for sporadic and late-onset familial AD (FAD) (Strittmafter et al., 1993). Later the ε3 allele of apoE was found to be a weaker risk factor for the disease. Expression of apoE mutants, especially the ε4 allele, together with the V717F mutant version of APP in mice increased the development of fibrillar deposits, neuritic plaques and neuritic degradation. Similar pathological hallmarks of AD were observed in mice expressing only the V717F mutant of APP, simply at an older age. The combination of the expression of the transgenes did not change the observed pathology of the disease, simply the time frame in which the pathology was observed. Expression of the V717F mutant version of APP in an $\text{apoE}^{-/-}$ knockout mouse resulted in an absence of neuritic degradation. This study demonstrated a clear role for ApoE in the pathology of AD, but did not provide a more accurate model of the disease than the singly transgenic mouse.

Transgenic mice expressing α-synuclein under control of the PDGFβ promotor have also been generated for use as a model of PD and LBD (Masliah et al., 2000). Neuronal expression of α-synuclein resulted in the progressive accumulation of α-synuclein and the development of inclusions in neurons in the neocortex, hippocampus and substantial nigra. Additionally electron-dense intranuclear deposits and cytoplasmic inclusions were observed. The mice demonstrated motor impairments which were associated with loss of dopaminergic terminals in the basal ganglia. However, no amyloid plaques, fibrillary tangles or cell death were observed.

A number of α-synuclein transgenic mice have also been generated. However, despite the use of different promoters (e.g. PDGFβ, Thy-1) as well as the use of both wild type and mutant forms (A30P and A53T) of α-synuclein, none of the mice provide a completely accurate model of PD. As with the various APP transgenic mice, differences were seen in the amount and location of protein expressed, depending on the promoter used and the site of insertion of the transgene into the genome. For example, when expression from the hα-synuclein transgene was driven by the PDGF-β promotor, the expression pattern of hα-synuclein most closely resembled that seen in normal brain or in diffuse LBD. Expression of hα-synuclein using a Thy-1 promoter resulted in higher expression of the transgene in a pattern more closely resembling the pattern of expression seen in PD. Higher expression resulted in more severe pathology. Mice expressing mutant versions of hα-synuclein developed hallmarks of disease earlier than those expressing the wild type version of the protein. Additionally, neurological dysfunction was dependent on the regions of the brain in which the protein was expressed.

Disease states are often the result of multiple changes in the organism, rather than a change in the expression level of a single protein or a single mutation within a gene. Although each of the transgenic animals described above had some hallmarks of AD, PD and/or LBD, none of them could serve as a complete model of any of the diseases. Not a single animal was found to have neurofibrillary tangles, a classic indicator of AD. The realization of the overlapping pathologies and occurrence of AD, PD and LBD emphasizes the need for an animal model that displays a more complete set of the pathologies and clinical manifestations of the diseases.

SUMMARY OF THE INVENTION

The invention is a transgenic mouse model with transgenes for expression of human β-amyloid peptides or hAPP and hα-synuclein. The transgenes may be wild type, mutant or truncated forms of the genes. The transgenes may be expressed under any of a number of promoters including the PDGF-β, Thy1 and prion (PrP) promoters. An intron, such as the SV40 intron, may be included in the transgene construct or the promotor, as in the case of the Thy1 promoter, the intron of the promoter may be used.

The mice of the present invention are generated by crossbreeding of mice carrying a single transgene for α-synuclein or hAPP. Applicants have generated a number of transgenic mouse lines overexpressing h α-synuclein (Masliah et al., 2000) and either wild-type or mutant forms of hAPP (Mucke et al, 2000) to elucidate the in vivo mechanism of amyloidogenesis in AD, PD and LBD. Additionally, there are a number of other hAPP transgenic mice available as referenced. Available mice include those expressing APP under control of the mouse or human Thy1 promoter (Andrää et al, 1996), the PDGF-β promoter (Games et al., 1995) with or without an SV40 intron, and the PrP (Borchelt et al., 1996; Hsia et al., 1999) promoter. The mice are well studied and characterized regarding regions of the brain and time frame in which the transgenes are expressed. Bigenic mice can readily be generated by crossing two mice that overexpress either hAPP or hα-synuclein in regions of the brain most effected by AD, PD or LBD as desired. Ideally the mice crossed should carry only one copy of the transgene such that littermates expressing both, either or neither transgene can be compared to each other. Overexpression of transgenes can be detected by any of a number of methods well known to one skilled in the art including, but not limited to, ribonuclease protection assay (RPA), Western blot, immunofluorescence, or like analysis, where the signal obtained is above background cross-reactivity with mouse RNA or protein found in non-transgenic littermates.

The bigenic PDGF-β-α-synuclein-PDGF-β-hAPP mice of the invention have been shown to express high levels of APP which is properly processed into Aβ fragments, in addition to exhibiting extracellular amyloidosis and neurofibrillary tangles which, in an age- and brain region-specific manner, morphologically resembles senile plaques seen in AD. Expression of hα-synuclein did not seem to alter the expression of hAPP. However, there was extensive accumulation of hα-synuclein in the bigenic mice as compared to the single hα-synuclein mice.

The functional and morphological alterations in the PDGF-β-α-synuclein-hAPP bigenic mice resembled the Lewy body variant of AD. Bigenic mice developed physiological and pathological hallmarks and impaired motor function more closely resembling human disease states as compared to singly transgenic mice. The effect of the combination of the expression of both genes is synergistic. The development of fibrillary α-synuclein inclusions, never before observed in rodents, but a standard hallmark of PD and LBD, were seen. Synaptic degeneration had been observed in both of the singly transgenic mice, but never neuronal cell death, which was seen in the bigenic mice. The bigenic mice had severe deficits in learning and memory, and developed motor deficits before PDGF-β-α-synuclein singly transgenic mice which display only minor, if any motor deficiencies. The onset of motor deficits began at 6 months with the bigenic mice, rather than at 12 months as is typically seen with the PDGF-β-hAPP mice. The bigenic mice showed the most prominent age-dependent degeneration of cholinergic neurons and presynaptic terminals as compared to their singly- or non-transgenic littermates. Although synaptic degeneration was observed in the singly transgenic mice, neuronal cell death was not observed in the singly transgenic littermates. hAPP-α-synuclein mice also had abundant β-amyloid plaques and an even greater number of α-synuclein-immunoreactive neuronal inclusions. Ultrastructurally, these inclusions were often fibrillar in double transgenic mice, but were amorphous in singly transgenic α-synuclein mice. This is the first demonstration of the presence of fibrillary Lewy-body like inclusions that were previously believed to not exist in rodents.

Additionally, the present invention is a method for the evaluation of the in vivo effects of α-synuclein with APP, in combination, on amyloidogenesis and neurodegeneration. Evaluation of the effects of the proteins in the development and progression of disease may be assessed by functional, pathological or biochemical assays, ideally in comparison to littermates carrying only a single or no transgene for either α-synuclein or hAPP. Studies with bigenic α-synuclein-hAPP mice demonstrate that hα-synuclein and hAPP/Aβ have distinct, as well as overlapping, pathogenic effects on the integrity and function of the brain. While hα-synuclein did not affect the Aβ-dependent development of neuritic plaques or the overall Aβ content in the brain, it worsened hAPP/Aβ-dependent cognitive deficits and neurodegeneration in specific brain regions. These findings indicate that hα-synuclein can enhance the toxicity of Aβ through plaque-independent mechanisms. They correlate well with clinical observations suggesting that people with the Lewy body variant of AD have a more rapid cognitive decline than people with pure AD. Overexpression of hAPP/Aβ, in turn, promoted the intraneuronal accumulation of hα-synuclein in transgenic mice and accelerated the development of motor deficits. In view of these pathogenic interactions between Aβ and hα-synuclein, drugs aimed at blocking the accumulation of Aβ or hα-synuclein will likely benefit a broader spectrum of neurodegenerative disorders than previously anticipated. Additionally, the bigenic mouse provides a better predictive model of the potential for an intervention to be useful to a patient.

DETAILED DESCRIPTION AND PREFERRED EMBODIMENTS

Figure 1:
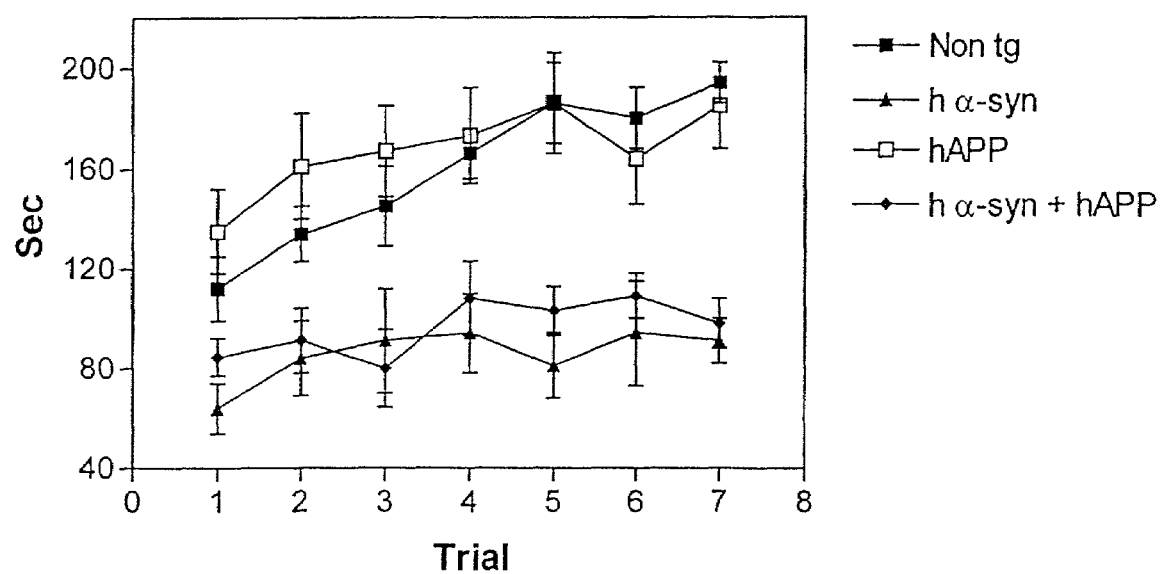
FIG. 1. Characterization of the motor deficits in the hSYN and the hAPP tg mice in the rotorod. Compared to non-transgenic littermates, singly-tg hSYN mice displayed significant motor deficits. Similarly, bigenic hSYN/hAPP mice showed levels of performance impairment similar to singly-tg hSYN mice. Mice expressing hAPP alone were not different from non-tg controls. N=6-8 per genotype, age 12 months.

The mechanisms by which altered expression and processing of α-synuclein or APP might lead to neurodegenerative disorders such as AD, PD and LBD remain somewhat unclear. It is generally understood that abnormal protein aggregation is a common feature in these disorders and that either full length α-synuclein, or protein fragments thereof, and Aβ are major constituents of these protein aggregates. In many disease states, multiple changes are required for the full onset of the condition. No animal models with single mutations in either APP or α-synuclein have provided accurate models of AD, PD or LBD. However, the bigenic PDGF-β-α-synuclein-PDGF-β-hAPP mouse displays hallmarks of these diseases that were not previously observed in either of the singly transgenic animals. By expressing both proteins, one gets a more accurate model of the disease. By using mice that express different levels of each protein, one can obtain a variety of models with different rates of onset and severity of disease. These will mimic the differences seen in humans.

Transgenic mice expressing hAPP or α-synuclein can be divided into two general categories of low expressing and high expressing strains. The classes can be further subdivided into mice that express wild type proteins that are less toxic than mutant proteins. For example, all mice expressing APP will eventually develop some plaques and some disease. However, the rate of development of plaques and resulting disease will be most rapid with mice expressing the Swedish double mutation at aa 670/671. Expression of hAPP with a single mutation at aa 717 will result in disease with fewer plaques in age matched animals. Similarly, different mutations and promoters will manifest various severity of disease in α-synuclein transgenic mice. Mice expressing hα-synuclein under the control of a Thy-1 promoter accumulate protein in the synapses and neurons throughout the brain, including the thalmus, basal ganglia, substantial nigra and brainstem. One line of mice expressing α-synuclein under the control of the PDGF-β promoter accumulate protein in synapses in the neocortex, limbic system and olfactory regions, as well as in inclusion bodies in neurons in deeper layers of the neurocortex. Another strain displayed α-synuclein expression in glial cells mimicking multiple system atrophy.

In order for the proteins to act synergistically to produce pathologies not seen in the singly transgenic mice, strains of mice that express the proteins in the same brain regions need to be mated. The production of $A\beta_{1-42}$ is clearly the driving force in the development of the LBD-like state in the bigenic mice. Expression of hAPP increases the accumulation of hα-synuclein. It also increases the severity of the disease and results in an earlier age of disease onset in the hα-synuclein transgenic mice. hα-Synuclein transgenic mice with no apparent disease develop disease upon crossing the mice with transgenic mice expressing an amyloidogenic version of APP. Crossing hα-synuclein mice with no apparent disease with mice expressing a non-amyloidogenic version of hAPP does not exacerbate the process of the development of disease. As spontaneous forms of AD, PD and LBD tend to have a relatively slow onset, suggesting low levels of mutant protein expression, crossing two strains that do not show significant disease alone provides a model for spontaneous onset of the diseases frequently seen in humans. Similarly, transgenic animals expressing APP at an earlier stage than α-synuclein mimic AD patients who later become demented. Transgenic animals expressing low levels of both proteins mimic spontaneous onset of the disease, which is slow in AD, PD and LBD. Brain regions of expression also serve as a motivation to cross specific transgenic strains. For example, mice expressing hAPP and hα-synuclein in regions of the brain most severely effected in LBD could be crossed to serve as a model for LBD.

Existing transgenic mice are selected based on criteria including level and brain region of protein expression, age of development of symptoms, neurological disorders and effect of background strain. Unlike transgenic mice that are generated by the insertion of constructs into mouse embryos that can result in a number of phenotypes, the mice of the invention are bigenic mice generated by the combination of mice with well known characteristics. Models are designed to most closely fit the disease of interest based on the criteria among those listed above. The expression of one protein is not disrupted by the expression of the other. The enhancement of the pathology of α-synuclein by co-expression of hAPP is now known. One skilled in the art may make rational decisions in combining known strains of mice to develop bigenic strains that most closely mimic the disease state of interest.

EXAMPLE 1

Generation of transgenic α-synuclein and hAPP mice. Transgenic mice are achieved routinely in the art using the technique of microinjection, as described in U.S. Pat. No. 4,736,866 issued to Leder et al., and as provided by B. Hogan et al. (1986). U.S. Pat. No. 5,574,206 issued to Jolicoeur particularly describes the creation of transgenic mice bearing functional HIV genes and their use in the modeling and study of HIV-mediated diseases. These references are herein incorporated by reference.

EXAMPLE 2

Figure 2:
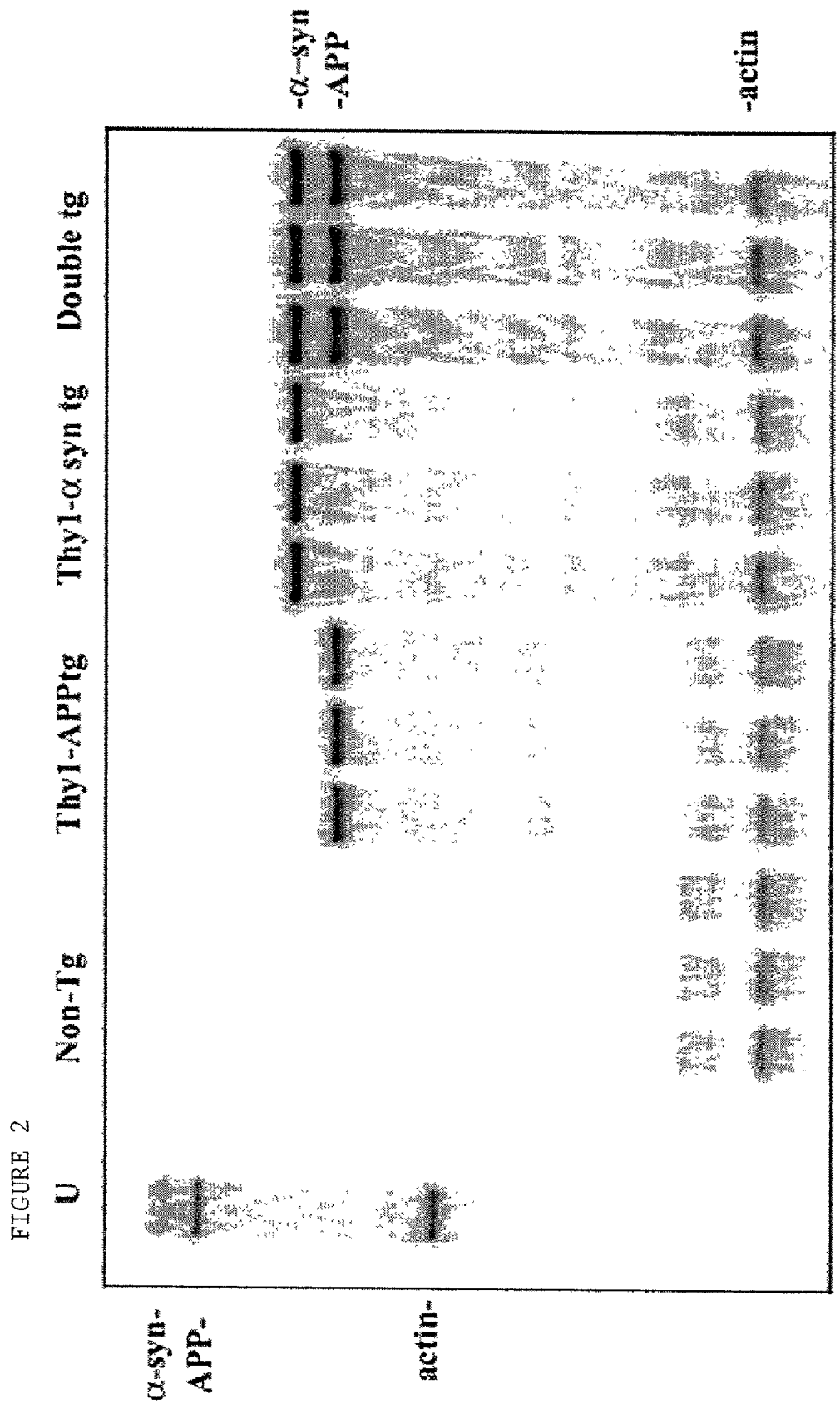
FIG. 2. RNase protection assay of total RNA from brains of transgenic and non-transgenic mice. Lane U represents undigested transcripts. The right hand side notation of the figure indicate the size of the digested samples. Sample lanes represent analysis of three separate mice each from Non-Tg, non-transgenic mice (i.e. control); Thy1-hAPPtg, transgenic mice; Thy1-α-syn'tg, transgenic mice; and double tg, transgenic mice containing both the human (h)APP751 and the α-synuclein genes.

Coexpression of hα-synuclein and hAPP in vivo. Transgenic mice in which neuronal expression of hα-synuclein (Masliah et al., 2000) or FAD-mutant hAPP (Mucke et al., 2000) is directed by the PDGFβ chain promoter have been described. Additionally, a number of other APP mice have been described including, but not limited to, those described in the present application. Lines with high levels of neuronal hα-synuclein (line D) or Aβ (line J9) production were selected. Crosses between heterozygous hα-synuclein and heterozygous hAPP mice from these lines yielded four groups of littermates: hα-synuclein mice (n=26), hAPP mice (n=32), hα-synuclein/hAPP mice (n=21), and nontransgenic controls (n=31). Levels of transgene-derived mRNAs in the brain were similar in singly and doubly transgenic mice, indicating that coexpression of hα-synuclein and hAPP did not alter transgene expression (FIG. 2). At the protein level, expression of hα-synuclein did not affect hAPP expression in doubly transgenic mice. However, there was a trend for cerebral hα-synuclein levels to be higher in hα-synuclein/hAPP mice than in hα-synuclein mice, which may reflect effects of Aβ on hα-synuclein accumulation.

EXAMPLE 3

Overexpression of human α-synuclein in bigenic mice enhances Alzheimer's disease-like neuropathology. It has been established that both α-synuclein and NAC are integral components of plaques formed in in vitro models of Alzheimer's disease. In order to determine how these molecules contribute to amyloidogenesis in vivo, specifically in the PDAPP bigenic mouse models, brain sections from effected bigenic mice were treated with formic acid and immunostained with antibodies against α-synuclein and NAC. The analysis of results confirm that, as in in vitro models of Alzheimer's disease, in the PDAPP bigenic mice, NAC is present in the amyloid core while α-synuclein is found in the dystrophic neurites. Additionally, neuropathological examination of PDAPP bigenic mice overexpressing α-synuclein revealed widespread astrogliosis in the neocortex and hippocampus accompanied by increased amyloid deposition, once again establishing that the increased expression of α-synuclein plays a key role in the pathogenesis of neurodegenerative conditions associated with amyloidogenesis. Therefore it was conclusively demonstrated that α-synuclein is critical for plaque formation in vivo and as such, constitutes a reasonable target for the design of anti-amyloidogenic compounds useful for in vivo therapies of Alzheimer's disease and other neurodegenerative conditions involving amyloid formation.

EXAMPLE 4

Neurological deficits in hα-synuclein/hAPP mice. Motor deficits were assessed with the rotarod test (FIG. 1). Consistent with previous observations, hα-synuclein mice developed age-dependent motor deficits. At 6 months of age, hα-synuclein/hAPP mice already showed deficits relative to nontransgenic controls ($P<0.03$ by repeated measures ANOVA), whereas hα-synuclein mice still performed normally. At 12 months of age, both hα-synuclein and hα-synuclein/hAPP mice showed deficits in this test compared with nontransgenic controls ($P<0.001$ by repeated measures ANOVA). hAPP mice had no significant motor deficits at either age. The severity of motor deficits was similar in 6-month-old hα-synuclein/hAPP and 12-month-old hα-synuclein and hα-synuclein/hAPP mice, suggesting that hAPP/Aβ accelerates the development of hα-synuclein-dependent motor deficits.

PDGF-hAPP mice have previously been shown to develop cognitive deficits. To determine the effects of hα-synuclein and hAPP/Aβ on spatial learning and memory, mice were assessed in a water maze test (Morris, 1984). In the sessions during which the target platform was visible, all groups of mice were able to locate the platform equally well, indicating that the motor deficits of hα-synuclein/hAPP do not preclude normal performance in the water maze test. In the hidden platform sessions, mice have to use their memory of the spatial relationship of the platform to visual cues outside of the maze to locate the submerged platform. In these sessions, hα-synuclein/hAPP mice showed the most significant learning deficits, whereas hα-synuclein mice and nontransgenic controls performed normally. hAPP mice tended to perform better than hα-synuclein/hAPP mice in the hidden platform sessions, but the difference was not statistically significant. The probe trial during which the platform is removed provides a putative measure of spatial memory retention. In the probe trial, hα-synuclein/hAPP mice and hAPP mice showed significantly less preference for the target quadrant than nontransgenic controls, suggesting impaired memory retention, whereas hα-synuclein mice were not impaired.

These results indicate that the motor deficits of hα-synuclein/hAPP mice are caused primarily by hα-synuclein, whereas their deficits in spatial learning and memory are caused primarily by hAPP/Aβ. Similar effects of hα-synuclein and hAPP/Ab may contribute to Lewy body diseases, which also combine motor and cognitive deficits.

EXAMPLE 5

Age-dependent neurodegeneration. Degeneration of cholinergic neurons in the nucleus basalis of Meynert results in major acquisition deficits in the water maze task in rodents. It is also a potentially important determinant of cognitive decline in AD and Lewy body diseases. Choline acetyltransferase (ChAT) mediates the synthesis of acetylcholine and serves as a marker of cholinergic neurons. The density of ChAT-immunoreactive neurons in the nucleus basalis of the transgenic models (n=12-13 mice/genotype, age range: 4-20 months) were determined. In hα-synuclein/hAPP mice, simple regression analysis revealed a highly significant inverse correlation between aging and the number of cholinergic neurons (R=0.828, P=0.0005). A trend toward such a correlation was present also in hα-synuclein mice (R=0.538, P=0.071) and hAPP mice (R=0.511, P=0.089), but not in nontransgenic controls (R=0.127, P=0.695). The greatest loss of cholinergic neurons was observed in hα-synuclein/hAPP mice, while more moderate losses were found in aged hAPP mice. These results are consistent with the observation that cholinergic deficits are more severe in human cases with the Lewy body variant of AD than in cases with pure AD. hα-Synuclein/hAPP mice and hAPP mice also had a significant loss of cholinergic neurons in the caudate/putamen, consistent with the decreased ChAT activity in the caudate of AD patients with or without Lewy bodies.

People with AD or the Lewy body variant of AD typically also develop a significant loss of synapses in the neocortex, which is reflected in decreased synaptophysin immunoreactivity. Synaptophysin-immunoreactive presynaptic terminals of defined signal intensity (SIPT) in the neocortex of 4- to 20-month-old mice (n=15-19/genotype) were measured. There was a significant inverse correlation between aging and neocortical SIPT levels in hAPP mice (R=0.744, P=0.0006) and hα-synuclein/hAPP mice (R=0.524, P=0.021), but not in hα-synuclein mice (R=0.479, P=0.071) or nontransgenic controls (R=0.151, P=0.564). At 20 months of age, SIPT levels in the neocortex (% area occupied, mean±SD, n=3-4 mice/genotype) were highest in nontransgenic controls (25.6±0.9) and lowest in hα-synuclein/hAPP mice (18.3±4.8, P<0.05 by Tukey-Kramer test), with values for hAPP mice (20.9±1.7) and hα-synuclein mice (23.0±0.9) falling in between. In contrast, SIPT levels in the caudate/putamen at 20 months of age (mean±SD, n=3-4 mice/genotype) were normal in nontransgenic mice (27.1±1.5) and hAPP mice (25.1±3.6), but decreased in hα-synuclein mice (21.0±0.9) and hα-synuclein/hAPP mice (20.1±1.7) (P<0.05 vs nontransgenic controls by Tukey-Kramer test).

These results suggest that the age-dependent loss of cholinergic neurons in hα-synuclein/hAPP mice depends primarily on hAPP/Aβ, with hα-synuclein having some additive effects in the nucleus basalis. The age-dependent loss of SIPT in the neocortex of these mice is also due primarily to hAPP/Aβ with minor contributions from hα-synuclein, whereas the loss of SIPT in the basal ganglia is due almost entirely to hα-synuclein.

EXAMPLE 6

Aβ promotes accumulation of hα-synuclein. Accumulation of hα-synuclein within neurons is a hallmark of Lewy body diseases, including the Lewy body variant of AD. Age-dependent accumulation of hα-synuclein in neurons of hα- synuclein singly transgenic mice has been previously observed (Masliah, 2000). Between 4 and 20 months of age, the number of neuronal inclusions in the neocortex was on average 1.6-fold higher in hα-synuclein/hAPP mice than in age-matched hα-synuclein mice (15.3±1.1 vs. 9.5±0.9 per mm$^2$, mean±SEM, P=0.0002 by unpaired two-tailed Student's t test, n=28-32 mice/genotype). This is illustrated for 12-month-old mice. The number of inclusions increased with age in both hα-synuclein and hα-synuclein/hAPP mice. These results indicate that hAPP/Aβ enhances the accumulation of hα-synuclein in neurons.

By ultrastructural analysis, all intraneuronal inclusions in hα-synuclein mice were amorphous and electrodense, whereas many of the intraneuronal inclusions in hα-synuclein/hAPP were fibrillar, increasing their resemblance to Lewy bodies in the human disease, which typically contain fibrillar elements. The filamentous inclusions in the neuronal cytoplasm were decorated with gold particles when brain sections of hα-synuclein/hAPP mice were analyzed by immunogold electron microscopy with anti-hα-synuclein or anti-Aβ. These results suggest that Aβ may promote the in vivo fibrillization of hα-synuclein by direct interaction. Further supporting this possibility, Aβ-immunoreactive granular deposits were detected by confocal microscopy in hα-synuclein-positive intraneuronal inclusions in hα-synuclein/hAPP mice.

To further evaluate whether the alterations observed in hα-synuclein/hAPP mice could indeed result from direct pathogenetic interactions between Aβ and hα-synuclein, in vivo analysis was extended to two in vitro models. In a cell-free system, both freshly solubilized and putatively aggregated (aged) human Aβ$_{1-42}$ strongly promoted the formation of high molecular weight polymers of hα-synuclein, consistent with previous observations. In contrast, the less fibrillogenic Aβ$_{1-40}$ did not affect hα-synuclein aggregation in vitro. Notably, Aβ$_{1-42}$ and Aβ$_{1-40}$ also differed in their effect on the intracellular accumulation of α-synuclein in neuronal cell cultures when added to the culture medium. Aβ$_{1-42}$ strongly increased the intracellular accumulation of α-synuclein, but Aβ$_{1-40}$ did not.

Overproduction of Aβ$_{1-42}$ within the endoplasmic reticulum and intermediate compartment may interfere with the processing of hα-synuclein enhancing its accumulation. However, cell culture data demonstrate that extracellular exposure to Aβ$_{1-42}$ is sufficient to induce the intracellular accumulation of hα-synuclein, whereas exposure to Aβ$_{1-40}$ is not. It is interesting in this context that incubation of cells with extracellular Aβ$_{1-42}$ disrupted the integrity of lysosomal membranes, whereas incubation of cells with Aβ$_{1-40}$ did not. Moreover, the association of soluble hα-synuclein with planar lipid bilayers results in extensive bilayer disruption. The combined action of Aβ$_{1-42}$ and hα-synuclein results in a leakiness of endosomal-lysosomal membranes, allowing for a direct interaction between Aβ$_{1-42}$ and hα-synuclein in the cytosol. Such an interaction would promote the intracellular accumulation of hα-synuclein. This effect of Aβ$_{1-42}$ on hα-synuclein is likely mediated by direct fibrillogenic interactions between these molecules or by free radicals. Aβ exerts oxidative stress and studies indicate that oxidative cross-linking of hα-synuclein contributes to the formation of Lewy bodies (Hashimoto et al., 1999; Lee et al., 2000).

In contrast to the prominent effects of hAPP/Aβ on hα-synuclein-associated pathology, hα-synuclein expression did not significantly alter the extracellular deposition of Aβ into plaques or the development of plaque-associated neuritic dystrophy in 8-, 12-, and 20-month-old hα-synuclein/hAPP mice compared with age-matched hAPP mice (n=3-4 mice per genotype and age). Twelve-month-old hAPP and hα-synuclein/hAPP mice had similar cerebral levels of Aβ$_{1-40}$ (4.3±0.88 vs 4.6±0.6) and Aβ$_{1-42}$ (248±48 vs 275±41) as determined by ELISA (mg/g of hemibrain, mean±SD, n=4-11 mice/genotype).

EXAMPLE 7

Total RNA from hemibrains or from dissected brain regions was isolated and then analyzed by a solution hybridization RNase protection assay and resolved on a acrylamide/urea/Tris/borate/EDTA gel (FIG. 2). Lane U represents undigested transcripts of the α-synuclein gene (α-syn), the Aβ precursor gene (APP) and actin (actin). The right hand side notation of the figure indicate the size of the digested samples. Sample lanes represent analysis of three separate mice each from Non-Tg, non-transgenic mice (i.e. control); Thy1-hAPPtg, transgenic mice expressing human (h)APP751 cDNA under the regulatory control of the murine (m)Thy-1 gene; They1-α-syn'tg, transgenic mice expressing human α-synuclein under the regulatory control of the muring (m)Thy-1 gene; and double tg, transgenic mice containing both the human (h)APP751 and the α-synuclein genes under the regulatory control of the murine (m)Thy-1 gene.

EXAMPLE 8

Crossbreeding of hα-synuclein or PDAPP-J9M tg mice with mα- or mβ-synuclein KO mice. To further confirm that the deletion of α-synuclein will result in suppression of Aβ deposits in bigenic mice, whereas, deletion of β-synuclein will result in the stimulation of Aβ deposits, knock out (KO) mice, having the genes encoding α-synuclein or β-synuclein deleted (Lexicon Genetics Inc., The Woodlands, Tex.) were crossed with heterozygous PDAPP-J9M tg mice. The following lines were generated: 1) (PDAPP−/−;mα-syn+/+), 2) (PDAPP−/−;mα-syn+/−), 3) (PDAPP+/−;mα-syn+/+), 4) (PDAPP+/−; mα-syn+/−), and 5) (PDAPP−/−; mα-syn−/−). Mouse genotype was determined by PCR using tail DNA. Subsequently, the (PDAPP+/−;mα-syn+/−) were intercrossed generating the following offspring: 1) (PDAPP+/+; mα-syn+/+), 2) (PDAPP+/+;mα-syn+/−), and 3) (PDAPP+/+;mα-syn−/−). The same breeding protocol was followed for the generation of bigenic hα-synuclein or PDAPP-J9M and mβ-synuclein KO mice.

The effect of α-synuclein and β-synuclein on amyloid deposition was evaluated in both the homozygous KO mice (PDAPP+/+;mα-syn−/−) and in the mice hemizygous for synuclein (PDAPP+/+;mα-syn+/−) utilizing the same rotorod and neuropathological analysis used in previous examples.

EXAMPLE 9

Crossbreeding of h α-synuclein or PDAPP-J9M tg mice with mice overexpressing h β-synuclein. Following standard crossbreeding protocol (Mucke et al., 1995), the contents of which are herein incorporated by reference, high expressor heterozygous β-synuclein mice were crossed with heterozygous α-synuclein or PDAPP-J9M tg mice resulting in the generation of: 1) non-tg littermates (PDAPP−/−; hα or βsyn−/−), 2) bigenic (PDAPP+/−and hβ-synuclein+/−), 3) bigenic (hα-synuclein +/−and hβ-synuclein +/−), 4) singly tg hAPP, and 5) singly tg hα-synuclein or β-synuclein. Mouse genotype was confirmed using PCR with tail DNA.

Because the original line of α-synuclein tg mice showed motor deficits when subjected to the rotorod, the bigenic crosses were evaluated in the same manner. Analysis of rotorod performance revealed that β-synuclein overexpression reduced the motor deficits in α-synuclein tg mice. Subsequent neuropathological analysis demonstrated that β-synuclein overexpression resulted in the reduction of neuronal inclusions. β-synuclein overexpression was also shown to result in the reduction of neuronal loss in the α-synuclein tg mice. These results further confirm that β-synuclein is active in vivo and that it constitutes a substance that has potential as an anti-Parkinsonian and anti-Alzheimer's therapeutic.

hα-Synuclein/hAPP bigenic mice have cognitive and motor alterations, loss of cholinergic neurons and SIPT, extensive amyloid plaques, and hα-synuclein-immunoreactive intraneuronal fibrillar inclusions. All of these features are also found in the Lewy body variant of AD. Collectively, Lewy body diseases are common neurodegenerative disorders, second only to AD. They comprise a heterogeneous group of diseases including PD, diffuse Lewy body disease, and the Lewy body variant of AD. Patients with Lewy body disease typically have Lewy bodies, parkinsonism and cognitive impairments. Approximately 25% of patients with AD develop frank parkinsonism, and hα-synuclein-immunoreactive Lewy body-like inclusions develop in most cases of sporadic AD and FAD, as well as in Down's syndrome, which is associated with early-onset AD. Moreover, Lewy bodies contain hAPP. These associations indicate that hAPP/Aβ plays a role in the formation of Lewy bodies and the development of Lewy body diseases.

Studies with the hAPP/hα-synuclein mice demonstrate that hα-synuclein and hAPP/Ab have distinct, as well as convergent, pathogenic effects on the integrity and function of the brain. While hα-synuclein did not affect the Aβ-dependent development of neuritic plaques or the overall Aβ content in the brain, it worsened hAPP/Aβ-dependent cognitive deficits and neurodegeneration in specific brain regions. These findings indicate that hα-synuclein enhances the toxicity of Aβ through plaque-independent mechanisms. These data explain clinical observations suggesting that people with the Lewy body variant of AD have a more rapid cognitive decline than people with pure AD. Overexpression of hAPP/Aβ, in turn, promoted the intraneuronal accumulation of hα-synuclein in transgenic mice and accelerated the development of motor deficits. These effects were most likely mediated by Aβ or another hAPP product, in vitro studies indicate that Aβ is the culprit. In view of these pathogenic interactions between Aβ and hα-synuclein, drugs aimed at blocking the accumulation of Ab or hα-synuclein will benefit a broader spectrum of neurodegenerative disorders than previously anticipated.

REFERENCES

Andrää, K., Abramowski, D., Duke, M., Probst, A., Wiederhold, K.-H., Büürki, K., Goedert, M., Sommer, B. & Staufenbiel, M. (1996) *Neurobiol. Aging* 17, 183-190.

Borchelt D R, Davis J, Fischer M, Lee M K, Slunt H H, Ratovitsky T, Regard J, Copeland N G, Jenkins N A, Sisodia S S, Price D L. (1996) A vector for expressing foreign genes in the brains and hearts of transgenic mice. *Genet Anal*. 13:159-63.

Carlson, G. A., Borchelt, D. R., Dake, A., Turner, S., Danielson, V., Coffin, J. D., Eckman, C., Meiners, J., Nilsen, S. P., Younkin, S. G. and Hsiao (1997) *Hum. Mol. Gen*. 6:1951-9.

Games, D., Adams, D., Alessandrini, R., Barbour, R., Berthelette, P., et al. (1995) *Nature (London)* 373, 523-528.

Giasson, B. I., Duda, J. E., Murray, I. V., Chen, Q., Souza, J. M., Hurtig, H. I., lschiropoulos, H., Trojanowski, J. Q., Lee, V. M. (2000) Oxidative damage linked to neurodegeneration by selective alpha-synuclein nitration in synucleinopathy lesions. *Science* 290:985-9.

Hashimoto, M., Hsu, L. J., Xia, Y., Takeda, A., Sisk, A., Sundsmo, M. and Masliah, E. (1999) Oxidative stress induces amyloid-like aggregate formation of NACP/α-synuclein in vitro. *Neuroreport* 10:717-21.

Higgins, L. S., Rodems, J. M., Catalano, R., Quon, D. & Cordell, B. (1995) *Proc. Natl. Acad. Sci. USA* 92, 4402-4406.

Hogan, B. et al. (1986) *Manipulating the Mouse Embryo: A Laboratory Manual*, Cold Spring Harbor Laboratory, Cold Spring Harbor, N.Y., USA.

Holtzman, D. M., Bales, K. R., Tenkova, T., Fagan, A.M., Parsadanian, M., Sartorius, L. J., Mackey, B. M., Olney, J., McKeel, D., Wozniak, D. and Paul, S. M. (2000) Apolipoprotein E isoform-dependent amyloid deposition and neuritic degradation in a mouse model of Alzheimer's disease. 97:2892-7.

Hsia, A. Y., Masliah, E., McConlogue, L., Yu, G.-Q., Tatsuno, G., Hu, K., Kholodenko, D., Malenka, R. C., Nicoll, R. A. and Mucke, L. (1999) Plaque independent disruption of neural circuits in Alzheimer's disease mouse models. *Proc Natl. Acad. Sci. USA* 96:3228-33.

Hsiao K K, Borchelt D R, Olson K, Johannsdottir R, Kift C, Yunis W, Xu S, Eckman C, Younkin S, Price D, et al.(1995) Age-related CNS disorder and early death in transgenic FVB/N mice overexpressing Alzheimer amyloid precursor proteins. *Neuron* 15:1203-18.

Hsiao, K., Chapman, P., Nilsen, S., Eckman, C., Harigaya, Y., Younkin, S., Yang, F. & Cole, G. (1996) *Science* 274, 99-102

Kammesheidt, A., Boyce, F. M., Spanoyannis, A. F., Cummings, B. J., Ortegon, M., Cotman, C., Vaught, J. L. & Neve, R. L. (1992) *Proc. Natl. Acad. Sci. USA* 89, 10857-10861.

Kang J, Lemaire H G, Unterbeck A, Salbaum J M, Masters C L, Grzeschik K H, Multhaup G, Beyreuther K, Muller-Hill B. (1987) The precursor of Alzheimer's disease amyloid A4 protein resembles a cell-surface receptor. *Nature* 325: 733-6.

Lamb, B. T., Sisodia, S. S., Lawler, A. M., Slunt, H. H., Kitt, C. A., Kearns, W. G., Pearson, P. L., Price, D. L. & Gearhart, J. D. (1993) *Nat. Genet*. 5, 22-30.

Masliah, E., Rockenstein, E. M., Veinbergs, I., Mallory, M., Hashimoto, M., Takeda, A., Sagara, Y., Sisk, A., Mucke, L. (2000) Dopaminergic loss and inclusion body formation in alpha-synuclein mice: Implications for neurodegenerative disorders. *Science* 287:1265-9.

Morris R. (1984) Developments of a water-maze procedure for studying spatial learning in the rat. *J. Neurosci. Meth*. 11:47-60.

Mucke, L., Masliah, E., Johnson, W. B., Ruppe, M. D., Alford, M., Rockenstein, E. M., Forss-Petter, S., Pietropaolo, M., Mallory, M. & Abraham, C. R. (1994) *Brain Res*. 666,151-167.

Mucke, L., Abraham, c. R., ruppe, M. D., Rockenstein, E. M., Toggas, S. M., Mallory. M., Alford, M. and Masliah, E. (1995) Protection against HIV-1 gp120-induced brain damage by neuronal overexpression of human amyloid precursor protein (hAPP) *J.Exp.Med*. 181: 1551-56.

Mucke, L., Masliah. E., Yu, G.-Q., Mallory, M., Rockenstein, E. M., Tatsuno, G., Hu, K., Kholodenko, D., Johnson-Wood, K. and McConlogue, L. (2000) *J. Neurosci*. 20:4050-8.

Quon, D., Wang, Y., Catalano, R., Scardina, J. M., Murakami, K. & Cordell, B. (1991) *Nature (London)* 352:239-241.

Rockenstein E M, McConlogue L, Tan H, Power M, Masliah E, Mucke L (1995) *J. Biol. Chem*. 270:28257-28267.

Strittmatter, W. J., Saunders, A. M., Schmechel, D., Pericak-Vance, M., Enghild, J., Salvesen, G. S. & Roses, A. D. (1993) Apolipoprotein E: High-Avidity Binding to β-Amyloid and Increased Frequency of Type 4 Allele in Late-Onset Familial Alzheimer Disease. *Proc. Natl. Acad. Sci. USA* 90:1977-81.

Sturchler-Pierrat, C., Ambramowski, D., Duke, M., Wiederhold, K. H., et al. (1997) *Proc. Natl. Acad. Sci. USA* 94:13287-92.

(in example 3)Mucke et al. (1995) *J.Exp.Med*. 181:1551-6

What is claimed is:

1. A transgenic mouse comprising:
    a first transgenic nucleotide sequence, integrated into the genome of said mouse, comprising a sequence encoding the wild-type human amyloid precursor protein (hAPP) 751 amino acid isoform (hAPP751) operably linked to a first promoter; and
    a second transgenic nucleotide sequence, integrated into the genome of said mouse, comprising a sequence encoding the wild-type human (h) α-synuclein operably linked to a second promoter;
    wherein the first and second transgenic nucleotide sequences are expressed, the first and the second promoter are neuron-active promoters, and as a result of expression of the hAPP751 and (h) α-synuclein, said transgenic mouse develops amyloidosis, neurofibrillary tangles and intraneuronal accumulation of (h) α-synuclein.

2. The transgenic mouse of claim 1, wherein said first promoter is a platelet-derived growth factor β (PDGF-β) promoter.

3. The transgenic mouse of claim 2, wherein a simian virus (SV)40 derived intron operably links said PDGF-β promoter to said first transgenic nucleotide sequence.

4. The transgenic mouse of claim 1, wherein said first promoter is a Thy1 promoter.

5. The transgenic mouse of claim 1, wherein said first promoter is a prion (PrP) promoter.

6. The transgenic mouse of claim 1, wherein said second promoter is a Thy1 promoter.

7. The transgenic mouse of claim 1, wherein said second promoter is a PrP promoter.

8. The transgenic mouse of claim 1, wherein said second promoter is a PDGF-β promoter.

9. The transgenic mouse of claim 8, wherein a SV40 derived intron operably links said PDGF-β promoter to said second transgenic nucleotide sequence.

10. The transgenic mouse of claim 1, wherein the nucleotide coding sequence of hAPP comprises an intron between exons 6 through 9 of the hAPP-encoding sequence.

11. A transgenic mouse comprising:
    a first transgenic nucleotide sequence, integrated into the genome of said mouse, comprising a sequence encoding the wild-type human amyloid precursor protein (hAPP) 751 amino acid isoform (hAPP751) operably linked to a platelet derived growth factor β (PDGF-β) promoter operably linked to a simian virus (SV) 40 intron; and
    a second transgenic nucleotide sequence, integrated into the genome of said mouse, comprising a sequence encoding the wildtype human (h) α-synuclein operably linked to a PDGF-β promoter operably linked to an SV40 intron;
    wherein the first and second transgenic nucleotide sequences are expressed, and as a result of expression of the hAPP751 and wildtype human (h) α-synuclein, said transgenic mouse develops amyloidosis, neurofibrillary tangles and intraneuronal accumulation of (h) α-synuclein.

12. The transgenic mouse of claim 11, wherein said transgenic mouse develops formation of intraneuronal inclusions characteristic of Lewy body disease.

13. The transgenic mouse of claim 11, wherein said transgenic mouse develops formation of fibrillary Lewy body-like inclusions.

14. The transgenic mouse of claim 11, wherein said transgenic mouse exhibits neuronal loss in the brain.

15. The transgenic mouse of claim 11, wherein said transgenic mouse develops a motor deficit.

16. The transgenic mouse of claim 11, wherein age of onset of the amyloidosis, neurofibrillary tangles and intraneuronal accumulation of (h) α-synuclein occurs at a significantly younger age, with $p<0.05$, than in a singly transgenic littermate, having only one of either the first or the second transgene.

17. A method for screening therapeutic agents for the prevention or treatment of neurological disease comprising
    (a) administering an agent to the transgenic mouse of claim 1; and,
    (b) determining the effect of the agent on amyloidosis, neurofibrillary tangles or intraneuronal accumulation of (h) α-synuclein in the transgenic mouse; and
    (c) comparing the effect to an untreated control mouse, wherein an improvement in any of these phenotypes indicates the agent is a therapeutic agent.

18. A method for screening for an agent for the prevention or treatment of intraneuronal accumulation of α-synuclein, amyloidosis or neurofibrillary tangles, comprising
    (a) providing a potential therapeutic agent;
    (b) administering the potential therapeutic agent of (a) to the transgenic mouse of claim 1, and
    (c) determining whether because of the administering of the potential therapeutic agent in (b) intraneuronal accumulation of α-synuclein, amyloidosis or neurofibrillary tangles in the transgenic mice is prevented or slowed by comparison to a control mouse not treated with the agent.

19. A method for screening therapeutic agents for the prevention or treatment of neurological disease comprising
    (a) administering an agent to the transgenic mouse of claim 11; and,
    (b) determining the effect of the agent on amyloidosis, neurofibrillary tangles or intraneuronal accumulation of (h) α-synuclein in the transgenic mouse; and
    (c) comparing the effect to an untreated control mouse, wherein an improvement in any of these phenotypes indicates the agent is a therapeutic agent.

20. A method for screening for an agent for the prevention or treatment of intraneuronal accumulation of α-synuclein, amyloidosis or neurofibrillary tangles, comprising
    (a) providing a potential therapeutic agent;
    (b) administering the potential therapeutic agent of (a) to the transgenic mouse of claim 11, and
    (c) determining whether because of the administering of the potential therapeutic agent in (b) intraneuronal accumulation of α-synuclein, amyloidosis or neurofibrillary tangles in the transgenic mice is prevented or slowed by comparison to a control mouse not treated with the agent.

* * * * *